United States Patent [19]

Richardson et al.

[11] Patent Number: 4,483,862

[45] Date of Patent: Nov. 20, 1984

[54] 2-(1H-1,2,4-TRIAZOL-1-YL)-1,1-BIS-(PER-FLUORO-ALKYL)ETHANOL ANTIFUNGAL AGENTS

[75] Inventors: Kenneth Richardson; Peter J. Whittle, both of Canterbury, England

[73] Assignee: Pfizer Inc., New York, N.Y.

[21] Appl. No.: 571,219

[22] Filed: Jan. 16, 1984

[30] Foreign Application Priority Data

Jan. 29, 1983 [GB] United Kingdom ............... 8302498

[51] Int. Cl.³ .................. A01N 43/64; A61K 31/41; C07D 249/08
[52] U.S. Cl. .................. 424/269; 260/456 R; 260/456 F; 260/456 P; 260/665 G; 548/262; 568/419; 568/842
[58] Field of Search ............... 424/269; 548/262

[56] References Cited

U.S. PATENT DOCUMENTS 4,243,405 1/1981 Balasubramanyan et al. ..... 424/245

FOREIGN PATENT DOCUMENTS 52424 5/1982 European Pat. Off. ............ 548/262
1464224 2/1977 United Kingdom ............... 548/262

Primary Examiner—Alton D. Rollins
Attorney, Agent, or Firm—Charles J. Knuth; Albert E. Frost; Paul D. Thomas

[57] ABSTRACT

Compounds of the formula

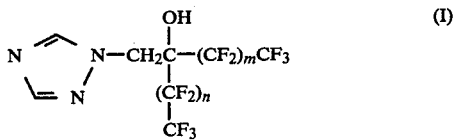

or a pharmaceutically or agriculturally acceptable acid addition salt thereof wherein m and n are independently 0, 1, 2, 3 or 4; method for their use in combatting fungal infections in plants, seeds and animals, including humans; and pharmaceutical and agricultural compositions containing said compounds or salts.

10 Claims, No Drawings

2-(1H-1,2,4-TRIAZOL-1-YL)-1,1-BIS-(PERFLUOROALKYL)ETHANOL ANTIFUNGAL AGENTS

BACKGROUND OF THE INVENTION

This invention relates to novel triazole derivatives which have antifungal activity and are useful in the treatment of fungal infections in animals, including humans, and as plant fungicides.

In European Patent Application No. 52,424 a class of antifungal compounds is disclosed which includes certain 2-(1H-1,2,4-triazol-1-yl)-1,1-dialkylethanols.

Our copending application, U.S. Ser. No. 517,183, filed July 25, 1983, discloses antifungal agents of the formula

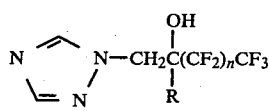

wherein n is an integer from 1 to 5 and R is phenyl, optionally substituted by certain groups, or is 5-chloro-2-pyridyl.

SUMMARY OF THE INVENTION

According to the invention, there are provided compounds of the formula

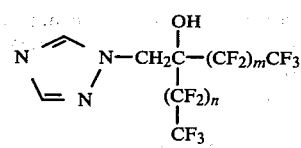

where
m is 0, 1, 2, 3 or 4; and
n is 0, 1, 2, 3 or 4;
and their pharmaceutically and agriculturally acceptable acid addition salts.

The invention also provides a pharmaceutical composition comprising an antifungal amount of a compound of the formula (I) or a pharmaceutically acceptable acid addition salt thereof, together with a pharmaceutically acceptable diluent or carrier.

The invention further provides a compound of the formula (I) or a pharmaceutically acceptable acid addition salt thereof, for use in medicine, in particular for treating fungal infections in animals, including humans.

The invention yet further provides a composition for use as an agricultural (including horticultural) fungicide suitable for use on a plant or seed which comprises an antifungal amount of a compound of the formula (I) or an agriculturally acceptable acid addition salt thereof, together with an agriculturally acceptable diluent or carrier.

The invention further provides a method of treating a fungal infection in an animal in need of such treatment which comprises administering to said animal an antifungal effective amount of a compound of formula (I) or pharmaceutically acceptable acid addition salt.

Yet further the invention provides a method of treating a fungal infection in a plant or seed in need of such treatment which comprises contacting said plant or seed, or the locus of said plant, with an antifungal effective amount of a compound or agriculturally acceptable salt according to claim 1.

Particularly preferred compounds of the invention are those wherein m is 0 or 1 and n is 1, 2 or 3 and especially preferred are the compounds of formula (I) where m and n have the respective values tabulated below.

| m | n |
|---|---|
| 0 | 2 |
| 1 | 1 |
| 1 | 2 |
| 1 | 3 |

Invention compounds where m and n have different values will contain an asymmetric center at the carbon atom bearing the hydroxy group. The invention includes each of the possible diastereomers of such compounds as well as their mixtures. Separation of diastereomeric pairs can be carried out by methods known to those of skill in the art, for example, by column chromatography.

DETAILED DESCRIPTION OF THE INVENTION

The compounds of formula (I) are prepared, for example, as shown below.

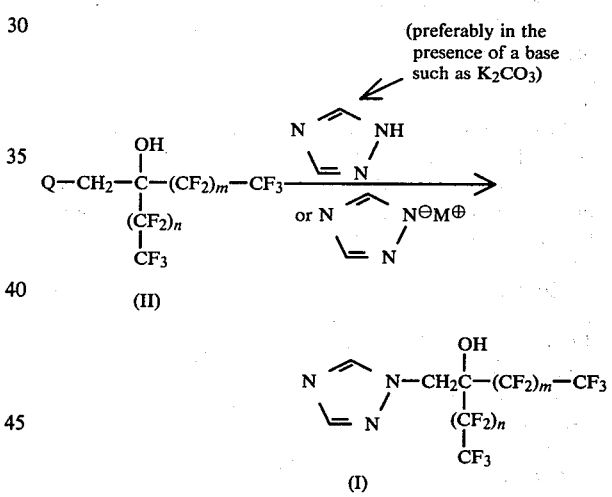

where Q is a leaving group, for example, Cl, Br, I, $CF_3SO_2O-$, $CH_3SO_2O-$ or p-toluenesulphonyloxy, and M is preferably Na, K or Li.

In a typical procedure, 1,2,4-triazole, the starting material (II) and potassium carbonate are heated together at a temperature in the range of about 50°–130° C., in the presence of a suitable organic solvent, e.g. dimethylformamide, until the reaction is complete, ordinarily in from 2–24 hours. The product (I) is then isolated and purified in a conventional manner. For example, the solvent is evaporated, the residue taken up in a water immiscible solvent, washed with water and the solvent evaporated to afford the product of formula (I) which can be further purified, if desired, e.g. by column chromatography.

The starting materials of the formula (II) are obtained in a conventional manner, e.g.

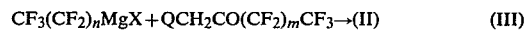

where X is Cl, Br or I, preferable Br or I and Q is as defined above, preferable Br. In a typical reaction the Grignard reagent is prepared at a subzero temperature in the presence of a dry ether solvent by contacting the corresponding perfluoroalkyl halide, $CF_3(CF_2)_nX$, with a molar excess of a commercially available Grignard reagent, e.g. phenylmagnesium bromide. An equimolar amount of the appropriate perfluoroalkylhalomethyl ketone (III) is then added and the mixture is stirred at low temperature, preferably $-80°$ to $-20°$ C., until the reaction is substantially completed. The reaction mixture is then quenched, e.g. by addition of water or acetic acid, and the desired product of formula (II) isolated by extraction.

The requisite starting compounds of formula (III) are either known compounds or are obtained by conventional synthetic methods well known to those of skill in the art, for example,

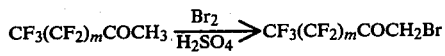

$$CF_3(CF_2)_mCOCH_3 \xrightarrow[H_2SO_4]{Br_2} CF_3(CF_2)_mCOCH_2Br$$

see, e.g. *J. Amer. Chem. Soc.*, 78, 2268–2270 (1956).

Pharmaceutically and agriculturally acceptable acid addition salts of the compounds of the formula (I) are those formed from strong acids which form non-toxic acid addition salts, such as hydrochloric, hydrobromic, sulphuric, oxalic and methanesulphonic acids.

The salts are obtained by conventional procedures, e.g. by mixing solutions containing equimolar amounts of the free base and desired acid, and the required salt is collected by filtration, if insoluble, or by evaporation of the solvent.

The compounds of the formula (I) and their pharmaceutically acceptable salts are antifungal agents, useful in combatting fungal infections in animals, including humans. For example they are useful in treating topical fungal infections in man caused by, among other organisms, species of Candida, Trichophyton, Microsporum or Epidermophyton, or in mucosal infections caused by *Candida albicans* (e.g thrush and vaginal candidiasis). They may also be used in the treatment of systemic fungal infections caused by, for example, *Candida albicans, Cryptococcus neoformans, Aspergillus fumigatus,* Coccidioides, Paracoccidioides, Histoplasma or Blastomyces.

The in vitro evaluation of the antifungal activity of the compounds can be performed by determining the minimum inhibitory concentration (m.i.c.) of the test compounds in a suitable medium at which growth of the particular microorganism fails to occur. In practice, a series of agar plates, each having the test compound incorporated at a particular concentration is inoculated with a standard culture of, for example, *Candida albicans* and each plate is then incubated for 48 hours at 37° C. The plates are then examined for the presence or absence of growth of the fungus and the appropriate m.i.c. value is noted. Other microorganisms used in such tests can include *Cryptococcus neoformans, Aspergillus fumigatus,* Trichophyton spp, Microsporum spp, *Epidermophyton floccosum, Coccidioides immitis* and *Torulopsis glabrata.*

The in vivo evaluation of the compounds can be carried out at a series of dose levels by intraperitoneal or intravenous injection or by oral administration, to mice which are inoculated with a strain of *Candida albicans*. Activity is based on the survival of a treated group of mice after the death of an untreated group of mice following 48 hours observation. The dose level at which the compound provides 50% protection against the lethal effect of the infection, the $PD_{50}$ in mg/kg, is noted.

Using the above test method, the following oral $PD_{50}$ values (mg/kg) were obtained with selected compounds of the invention in mice infected with

| *Candida albicans:* | |
|---|---|
| Compound of Example No. | Oral $PD_{50}$ (mg/kg) |
| 1 | 0.1 |
| 2 | ca. 40 |
| 3 | <1.0 |
| 4 | 2.2 |
| 5 | <1.0 |

For human use, the antifungal compound of formula (I), or a pharmaceutically acceptable acid addition salt thereof, can be administered alone, but will generally be administered in admixture with a pharmaceutical carrier selected with regard to the intended route of administration and standard pharmaceutical practice. For example, they can be administered orally in the form of tablets containing such excipients as starch or lactose, or in capsules or ovules either alone or in admixture with excipients, or in the form of elixirs or suspensions containing flavoring or coloring agents. They can be injected parenterally, for example, intravenously, intramuscularly or subcutaneously. For parenteral administration, they are best used in the form of a sterile aqueous solution which may contain other substances, for example, enough salts or glucose to make the solution isotonic with blood.

For oral and parenteral administration to human patients, the daily dosage level of the antifungal compounds of the formula (I) will be from 0.1 to 10 mg/kg (in divided doses) when administered by either the oral or parenteral route. Thus tablets or capsules of the compounds will contain from 5 mg to 0.5 g of active compound for administration singly or two or more at a time as appropriate. The physician in any event will determine the actual dosage which will be most suitable for an individual patient and it will vary with the age, weight and response of the particular patient. The above dosages are exemplary of the average case; there can, of course, be individual instances where higher or lower dosage ranges are merited, and such are within the scope of this invention.

Alternatively, the antifungal compounds of the formula (I) can be administered in the form of a suppository or pessary, or they can be applied topically in the form of a lotion, solution, cream, ointment or dusting powder. For example, they can be incorporated into a cream consisting of an aqueous emulsion of polyethylene glycols or liquid paraffin; or they can be incorporated, at a concentration of from 1 to 10%, into an ointment consisting of a white wax or white soft paraffin base together with such stabilizers and preservatives as may be required.

The compounds of the formula (I) and their salts also have activity against a variety of plant pathogenic fungi, including for example various rusts, mildews and moulds, and the compounds are thus useful for treating plants and seeds to eradicate or prevent such diseases.

The in vitro evaluation of the activity of the compounds against plant fungi can be determined by measuring their minimum inhibitory concentrations in the same way as previously described except that the plates are incubated at 30° C. for 48 hours or longer before being examined for the presence or absence of growth.

Microorganisms used in such tests include *Cochliobolus carbonum, Pyricularia oryzae, Glomerella cingulata, Penicillium digitatum, Botrytis cinerea* and *Rhizoctonia solani*.

For agricultural and horticultural purposes the compounds and their agriculturally acceptable acid addition salts are preferably used in the form of a composition formulated as appropriate to the particular use and purpose desired. Thus the compounds may be applied in the form of dusting powders, or granules, seed dressings, aqueous solutions, dispersions or emulsions, dips, sprays, aerosols or smokes. Compositions may also be supplied in the form of dispersible powders, granules or grains, or concentrates for dilution prior to use. Such compositions may contain such conventional carriers, diluents or adjuvants as are known and acceptable in agriculture and horticulture and they are manufactured in accordance with conventional procedures. The compositions may also incorporate other active ingredients, for example, compounds having herbicidal or insecticidal activity or a further fungicide. The compounds and compositions can be applied in a number of ways, for example they can be applied directly to the plant foliage, stems, branches, seeds or roots or to the soil, or other growing medium, and they may be used not only to eradicate disease, but also prophylactically to protect the plants or seeds from attack.

The following Examples illustrate the invention. All temperatures are in °C. Ratios of solvent mixtures are by volume. Percentages are by weight unless otherwise noted.

EXAMPLE 1

Decafluoro-2-(1H-1,2,4-triazol-1-ylmethyl)pentan-2-ol

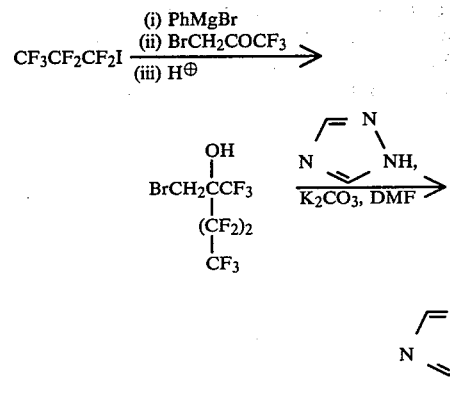

All stages of this reaction were carried out under nitrogen.

(A) Heptafluoropropyl iodide (5 g, 16.9 mmole) was stirred in dry diethyl ether (20 ml) at −78° C. Phenylmagnesium bromide (10 ml of a 1.88M solution in ether) was then added dropwise, keeping the temperature below −65° C. When the addition was complete, the reaction mixture was stirred at −20° C. for one hour. It was then cooled to −78° C. and 3-bromo-1,1,1-trifluoropropanone (4.87 g, 18.0 mmole) in dry diethylether (20 ml) was added dropwise, keeping the temperature below −65° C. When the addition was complete, the mixture was stirred at between −20° and −50° C. for four hours. Glacial acetic acid (3 ml) in diethyl ether (5 ml) was then added slowly, followed by water (15 ml). The mixture was then allowed to warm to 5° C. and the phases were separated. The aqueous phase was washed with ether (2×25 ml). The ethereal extracts were combined, dried (MgSO$_4$) and evaporated to give crude 2-bromomethyl-decafluoropentan-2-ol (5.0 g).

(B) The crude pentanol from part (A) (5.0 g, 13.8 mmole) was combined with 1,2,4-triazole (6 g), anhydrous potassium carbonate (18 g) and dry dimethylformamide (DMF) (60 ml), and the mixture was heated with stirring at 80° C. overnight. The DMF was then removed and water (100 ml) and ethyl acetate (75 ml) were added to the residue. The phases were separated and the aqueous phase was extracted with ethyl acetate (2×75 ml). The ethyl acetate extracts were combined, washed with water (100 ml), dried (MgSO$_4$) and evaporated. Purification of the residue by flash chromatography on silica (230–400 mesh) eluting with, firstly methylene chloride/methanol/ammonia (93:7:1 by volume) and secondly with ethyl acetate/hexane (7:1 by volume) gave, after trituration with hexane, the title compound. This was recrystallized from a mixture of methylene chloride and hexane to give 130 mg of the pure product, melting point 99°–101° C.

Analysis %: Found: C, 27.9; H, 1.4; N, 12.1; Calculated for C$_8$H$_5$N$_3$F$_{10}$O: C, 27.5; H, 1.4; N, 12.0.

EXAMPLES 2 TO 5

The following compounds were prepared similarly to the procedure of Example 1(A) and (B) from appropriate starting materials with the differences noted below:

$$N \diagup\!\!\!\!\diagdown N-CH_2\underset{\underset{CF_3}{\overset{(CF_2)_n}{|}}}{\overset{\overset{OH}{|}}{C}}-(CF_2)_mCF_3 \quad (I)$$

| Example No. | m | n | m.p. (°C.) | Analysis % (Theoretical in brackets) | | |
|---|---|---|---|---|---|---|
| | | | | C | H | N |
| 2 | 0 | 3 | gum | 27.4 (27.1) | 1.4 1.3 | 10.7 (10.5) |
| 3 | 1 | 3 | 62–63 | 27.3 (26.7) | 1.2 1.1 | 9.3 (9.4) |
| 4 | 1 | 1 | 67–71 | 27.6 (27.5) | 1.5 1.4 | 11.9 (12.0) |
| 5 | 1 | 2 | 67–70 | 27.0 (27.1) | 1.2 1.3 | 10.4 (10.5) |

In Examples 2 and 3, the reaction mixture in part (A) was quenched with 10% aqueous ammonium chloride solution in place of glacial acetic acid/ether/water, and in Examples 4 and 5, 30% aqueous ammonium chloride was used. In Examples 3 and 5 part (A), methylmagnesium bromide was used in place of phenylmagnesium bromide. Also, in part (A) of all the Examples, the temperature of the reaction mixture after the addition of the bromoketone was maintained at −30° C. instead of between −20° and −50° C.

EXAMPLE 6

Similarly, compounds of the formula shown in Examples 2-5, above, are prepared where m and n have the values tabulated below.

| m | n |
|---|---|
| 0 | 4 |
| 0 | 1 |
| 1 | 4 |
| 2 | 2 |
| 2 | 3 |
| 3 | 3 |
| 3 | 4 |
| 4 | 4 |

EXAMPLE 7

The following illustrate pharmaceutical compositions for the treatment of fungal infections:

(a) Capsule: 71 parts by weight of the compound of Example 1 are granulated with 3 parts maize starch and 22 parts lactose and then a further 3 parts maize starch and 1 part magnesium stearate are added. The mixture is regranulated and filled into hard gelatin capsules.

(b) Cream: 2 parts by weight of the compound of Example 5 are dissolved in 10 parts of propylene glycol and mixed into 88 parts of a vanishing cream base.

(c) Pessary: 2 parts by weight of the compound of Example 3 are suspended in 98 parts of a warm liquified suppository base which is poured into moulds and allowed to solidify.

We claim:

1. A compound of the formula $$N\underset{N}{\overset{}{\rightleftharpoons}} N-CH_2\underset{\underset{CF_3}{|}}{\overset{\overset{OH}{|}}{C}}-(CF_2)_mCF_3 \qquad (I)$$

or a pharmaceutically or agriculturally acceptable acid addition salt thereof,
where
m is 0, 1, 2, 3 or 4; and
n is 0, 1, 2, 3 or 4.

2. A compound as claimed in claim 1, wherein m is 0 or 1 and n is 1, 2 or 3.

3. The compound according to claim 2 wherein m is 0 and n is 2.

4. The compound according to claim 2 wherein m and n are each 1.

5. The compound according to claim 2 wherein m is 1 and n is 2.

6. The compound according to claim 2 wherein m is 1 and n is 3.

7. A pharmaceutical composition comprising an antifungal amount of a compound or pharmaceutically acceptable salt according to claim 1 and a pharmaceutically acceptable diluent.

8. An agricultural antifungal composition suitable for use on a plant or seed which comprises an antifungal amount of a compound or agriculturally acceptable salt according to claim 1 and an agriculturally acceptable diluent.

9. A method of treating a fungal infection in an animal in need of such treatment which comprises administering to said animal an antifungal effective amount of a compound or pharmaceutically acceptable salt according to claim 1.

10. A method of treating a fungal infection in a plant or seed in need of such treatment which comprises contacting said plant or seed, or the locus of said plant, with an antifungal effective amount of a compound or agriculturally acceptable salt according to claim 1.

* * * * *